(12) United States Patent
Schmidt et al.

(10) Patent No.: US 12,246,969 B2
(45) Date of Patent: Mar. 11, 2025

(54) SYNTHESIS OF TON FRAMEWORK TYPE MOLECULAR SIEVES

(71) Applicant: CHEVRON U.S.A. INC., San Ramon, CA (US)

(72) Inventors: Joel Edward Schmidt, Oakland, CA (US); Adeola Florence Ojo, Pleasant Hill, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 18/089,676

(22) Filed: Dec. 28, 2022

(65) Prior Publication Data

US 2023/0135430 A1    May 4, 2023

Related U.S. Application Data

(62) Division of application No. 17/173,712, filed on Feb. 11, 2021, now Pat. No. 11,565,943.

(51) Int. Cl.
*B01J 29/74* (2006.01)
*C01B 39/02* (2006.01)
*C01B 39/48* (2006.01)
*C10G 49/08* (2006.01)

(52) U.S. Cl.
CPC .......... *C01B 39/48* (2013.01); *B01J 29/7484* (2013.01); *C01B 39/02* (2013.01); *C01B 39/026* (2013.01); *C10G 49/08* (2013.01); *C10G 2300/4006* (2013.01); *C10G 2300/4012* (2013.01); *C10G 2300/4018* (2013.01)

(58) Field of Classification Search
None
See application file for complete search history.

(56) References Cited

U.S. PATENT DOCUMENTS

| | | | |
|---|---|---|---|
| 5,871,650 A * | 2/1999 | Lai | B01J 37/0246 585/818 |
| 2017/0113940 A1* | 4/2017 | Lobo | C01B 39/145 |
| 2017/0225959 A1* | 8/2017 | Maurer | C01B 39/087 |
| 2019/0176137 A1* | 6/2019 | Sontyana | C07C 5/2708 |

* cited by examiner

*Primary Examiner* — Sheng H Davis

(57) ABSTRACT

A method is disclosed making a molecular of TON framework type having unique properties. The method uses 1,3,4-trimethylimidazolium cations as a structure directing agent and a combined source of silicon and aluminum selected from alumina-coated silica and aluminosilicate zeolites. The obtained molecular sieve can be used in processes for dewaxing paraffinic hydrocarbon feedstocks.

5 Claims, 18 Drawing Sheets

SYNTHESIS OF TON FRAMEWORK TYPE MOLECULAR SIEVES

CROSS-REFERENCE TO RELATED APPLICATIONS

This application is a divisional application of U.S. patent application Ser. No. 17/173,712, filed on Feb. 11, 2021. The relevant disclosure of the above application is incorporated herein by reference in its entirety.

FIELD

This disclosure relates to an improved method for making molecular sieves having the TON framework structure and the use of molecular sieves so made in processes for catalytic conversion of hydrocarbon compounds.

BACKGROUND

Molecular sieve materials are classified by the Structure Commission of the International Zeolite Association according to the rules of the IUPAC Commission on Zeolite Nomenclature. According to this classification, framework type zeolites and other crystalline microporous crystalline materials, for which a structure has been established, are assigned a three-letter code and are described in the "*Atlas of Zeolite Framework Types*", Sixth Revised Edition, Elsevier (2007).

One known molecular sieve for which a structure has been established is the material designated as TON, which is a molecular sieve having a unique one-dimensional 10-membered ring channel system. Examples of TON framework type molecular sieves include ISI-1, KZ-2, NU-10, Theta-1, and ZSM-22. TON framework type materials are of significant commercial interest because of their activity as catalysts in dewaxing of paraffinic hydrocarbons.

According to the present disclosure, using 1,3,4-trimethylimidazolium cations as a structure directing agent and aluminosilicate starting materials, it has now been found that TON-type molecular sieves can be synthesized by simpler processes and in shorter heating periods than was previously possible. Using these materials, TON-type molecular sieves can be made prepared having unique morphologies and physico-chemical properties. In addition, it is possible to produce TON-type molecular sieves with small crystal size.

SUMMARY

In a first aspect there is provided a method of synthesizing a molecular sieve of TON framework type, the method comprising: (1) forming a reaction mixture comprising: (a) a combined source of silicon and aluminum, where the combined source of silicon and aluminum is an alumina-coated silica, an aluminosilicate zeolite of FAU framework type, or a mixture thereof; (b) a structure directing agent (Q) comprising 1,3,4-trimethylimidazolium cations; (c) a source of hydroxide ions; (d) water; and (e) seeds; and (2) subjecting the reaction mixture to crystallization conditions sufficient to form crystals of the molecular sieve.

In a second aspect, there is provided a molecular sieve of TON framework type and, in its as-synthesized form, comprising 1,3,4-trimethylimidazolium cations in its pores.

In a third aspect, there is provided a process for hydroisomerization of a paraffinic hydrocarbon feedstock, the process comprising: contacting the paraffinic hydrocarbon feedstock at hydroisomerization conditions with hydrogen and a catalyst comprising a molecular sieve of TON framework type, and yielding a product having an increase in branched hydrocarbons relative to hydrocarbon feedstock; wherein the catalyst further comprises 0.01 to 10% by weight of a noble metal.

DETAILED DESCRIPTION

Definitions

Figure 1:
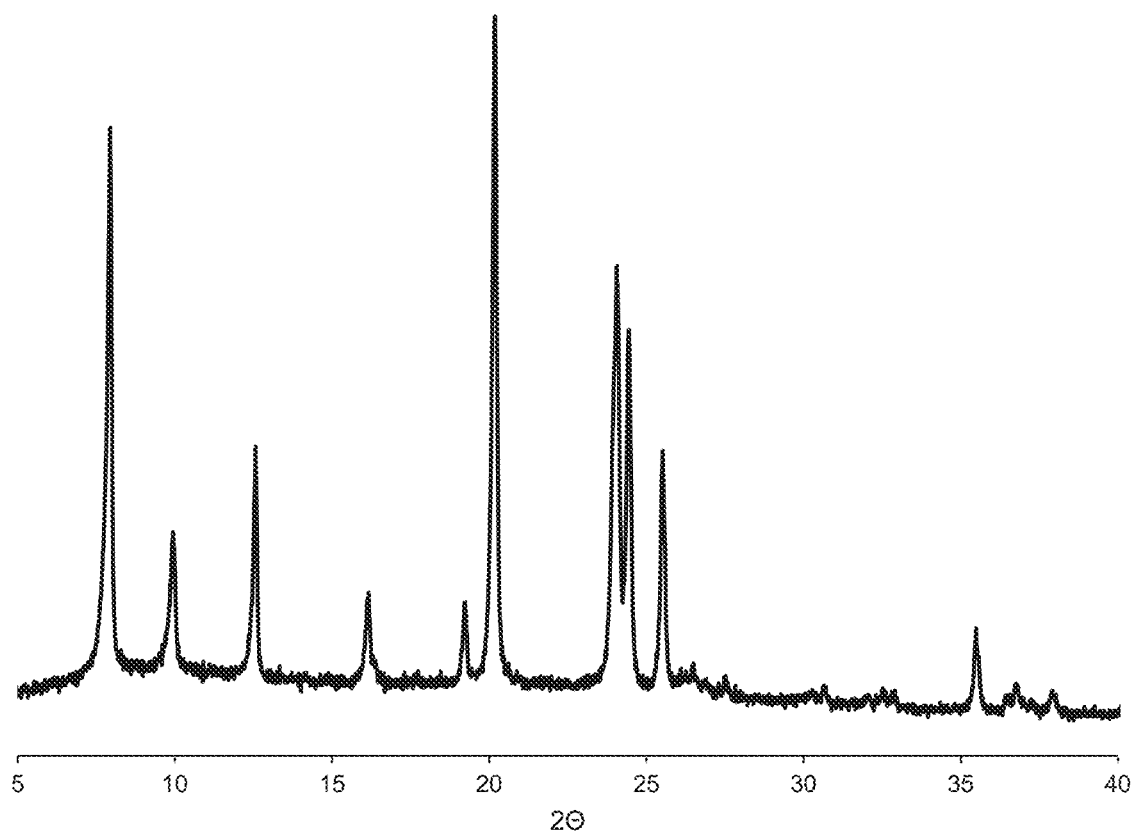
FIG. 1 shows a powder X-ray diffraction (XRD) pattern of the calcined molecular sieve obtained in Example 1.

The term "framework type" as used herein has the meaning described in the "*Atlas of Zeolite Framework Types*" by Ch. Baerlocher, L. B. McCusker and D. H. Olson (Elsevier, Sixth Revised Edition, 2007).

The term "as-synthesized" refers to a molecular sieve in its form after crystallization, prior to removal of the structure directing agent.

The term "Cn" hydrocarbon means a hydrocarbon compound having n number of carbon atom(s) per molecule. The term "Cn+" hydrocarbon means a hydrocarbon compound having n or more than n carbon atom(s) per molecule. The term "Cn−" hydrocarbon means a hydrocarbon compound having no more than n carbon atom(s) per molecule.

The term "$SiO_2/Al_2O_3$ molar ratio" may be abbreviated as "SAR".

Synthesis of the Molecular Sieve

A molecular sieve of TON framework type can be synthesized by: (1) forming a reaction mixture comprising: (a) a combined source of silicon and aluminum, where the combined source of silicon and aluminum is an alumina-coated silica, an aluminosilicate zeolite of FAU framework type, or a mixture thereof; (b) a structure directing agent (Q) comprising 1,3,4-trimethylimidazolium cations; (c) a source of hydroxide ions; (d) water; and (e) seeds; and (2) subjecting the reaction mixture to crystallization conditions sufficient to form crystals of the molecular sieve.

The reaction mixture can have a composition, in terms of molar ratios, within the ranges set forth in Table 1:

TABLE 1

|  | Broadest | Secondary |
|---|---|---|
| $SiO_2/Al_2O_3$ | 30 to 170 | 35 to 130 |
| $Q/SiO_2$ | 0.03 to 0.50 | 0.04 to 0.30 |
| $OH/SiO_2$ | 0.05 to 1.00 | 0.10 to 0.50 |
| $H_2O/SiO_2$ | 5 to 100 | 10 to 50 | wherein Q comprises 1,3,4-trimethylimidazolium cations.

The alumina-coated silica can have a $SiO_2/Al_2O_3$ molar ratio of at least 30 (e.g., 30 to 170, 35 to 100, 50 to 100, 60 to 80, or 100 to 170). Alumina-coated silicas may be obtained from Nalco. The aluminosilicate zeolite of FAU framework type can be zeolite Y. The aluminosilicate zeolite can have a $SiO_2/Al_2O_3$ molar ratio of at least 30 (e.g., 30 to 100, or 60 to 80). Examples of suitable aluminosilicate zeolites include Y zeolites CBV720, CBV760, and CBV780, available commercially from Zeolyst International. The combined source of silicon and aluminum may be used as the sole or predominant source of silicon and aluminum in the reaction mixture.

The reaction mixture can contain a separate source of silicon. If present, suitable sources of silicon include colloidal silica, precipitated silica, fumed silica, alkali metal silicates, and tetraalkyl orthosilicates.

The source of hydroxide ions can be an alkali metal hydroxide. The alkali metal can be lithium, sodium, potassium, or a mixture thereof. However, this component can be omitted so long as the equivalent basicity is maintained. The structure directing agent can be used to provide hydroxide ion. If present, the molar ratio of alkali metal cation/$SiO_2$ can be in a range of from 0.05 to 1.00 (e.g., 0.05 to 0.50).

The structure directing agent (Q) comprises 1,3,4-trimethylimidazolium cations, represented by the following structure (1):

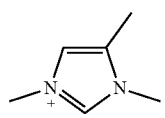

(1)

Suitable sources of Q include the hydroxides, chlorides, bromides, and/or other salts of the quaternary ammonium compound.

The reaction mixture also contains seeds, typically of a TON framework type molecular sieve, desirably in an amount of from 0.01 to 10,000 ppm by weight (e.g., 100 to 5000 ppm by weight) of the reaction mixture. Seeding can be advantageous to improve selectivity for TON and/or to shorten the crystallization process.

Crystallization of the desired molecular sieve from the above reaction mixture can be carried out under either static, tumbled or stirred conditions in a suitable reactor vessel, such as for example polypropylene jars or Teflon-lined or stainless-steel autoclaves, at a temperature of from 120° C. to 200° C. (e.g., 135° C. to 180° C.) for a time sufficient for crystallization to occur at the temperature used, e.g., from about 1 day to 10 days (e.g., 2 days to 7 days). Crystallization is usually conducted under pressure in an autoclave so that the reaction mixture is subject to autogenous pressure.

Once the desired molecular sieve crystals have formed, the solid product can be separated from the reaction mixture by standard mechanical separation techniques such as centrifugation or filtration. The recovered crystals are water-washed and then dried, for several seconds to a few minutes (e.g., 5 seconds to 10 minutes for flash drying) or several hours (e.g., 4 hours to 24 hours for oven drying at 75° C. to 150° C.), to obtain the as-synthesized molecular sieve crystals. The drying step can be performed under vacuum or at atmospheric pressure.

As a result of the crystallization process, the recovered crystalline molecular sieve product contains within its pores at least a portion of the structure directing agent used in the synthesis.

The as-synthesized molecular sieve may be subjected to thermal treatment, ozone treatment, or other treatment to remove part or all of the structure directing agent used in its synthesis. Removal of structure directing agent may be carried out using thermal treatment (e.g., calcination) in which the as-synthesized material is heated in an atmosphere selected from air, nitrogen, or a mixture thereof at a temperature sufficient to remove part or all of the structure directing agent. While sub-atmospheric pressure may be used for the thermal treatment, atmospheric pressure is desired for reasons of convenience. The thermal treatment may be performed at a temperature at least 370° C. (e.g., 400° C. to 700° C.) for at least a minute and generally not longer than 20 hours (e.g., 1 to 8 hours).

The TON-type molecular sieve (where part or all of the structure directing agent is removed) may be combined with a hydrogenating metal component. The hydrogenating metal component may be selected from molybdenum, tungsten, rhenium, nickel, cobalt, chromium, manganese, or a noble metal, such as platinum or palladium where a hydrogenation-dehydrogenation function is to be performed. Such hydrogenating metal components may be incorporated into the composition by way of one or more of the following processes: co-crystallizing; ion-exchanging into the composition; impregnating therein or physically admixing therewith. The amount of metal can be in a range of 0.001 to 20% by weight (0.01 to 10% by weight, or 0.5 to 2.0% by weight) of catalyst.

Once the molecular sieve has been synthesized, it can be formulated into a catalyst composition by combination with another material resistant to the temperatures and other conditions employed in organic conversion processes. Such resistant materials may be selected from active materials, inactive materials, synthetic zeolites, naturally occurring zeolites, inorganic materials, or a mixture thereof. Examples of such resistant materials may be selected from clays, silica, titania, metal oxides such as alumina, or a mixture thereof. The inorganic material may be either naturally occurring, or in the form of gelatinous precipitates or gels, including mixtures of silica and metal oxides. Use of a resistant material in conjunction with the molecular sieve, i.e., combined therewith or present during synthesis of the as-synthesized material, which crystal is active, tends to change the conversion and/or selectivity of the catalyst in certain organic conversion processes. Inactive resistant materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. The inactive resistant materials (i.e., clays, oxides, etc.) function as binders for the catalyst. A catalyst having good crush strength can be beneficial because in commercial use it is desirable to prevent the catalyst from breaking down into powder-like materials.

Naturally occurring clays which may be composited with the molecular sieve include the montmorillonite and kaolin family, which families include the subbentonites, and the kaolins commonly known as Dixie, McNamee, Ga. and Florida clays or others in which the main mineral constituent is halloysite, kaolinite, dickite, nacrite, or anauxite. Such clays may be used in the raw state as originally mined or initially subjected to calcination, acid treatment or chemical modification.

Binders useful for compositing with the molecular sieve also include inorganic oxides selected from silica, zirconia, titania, magnesia, beryllia, alumina, or a mixture thereof.

In addition to the foregoing materials, the molecular sieve may be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of molecular sieve and inorganic oxide matrix may vary widely, with the molecular sieve content ranging from 1 to 95% by weight (e.g., 20 to 90% by weight) of the composite.

The catalyst is employed in the conventional manner in the form of, for example, spheres or extrudates.

Characterization of the Molecular Sieve

In its as-synthesized and anhydrous form, the molecular sieve can have a chemical composition, in terms of molar ratios, within the ranges set forth in Table 2:

TABLE 2

| | Broadest | Secondary |
|---|---|---|
| $SiO_2/Al_2O_3$ | 30 to 100 | 35 to 80 |
| $Q/SiO_2$ | >0 to ≤0.1 | >0 to ≤0.1 | wherein Q comprises 1,3,4-trimethylimidazolium cations.

The TON framework type molecular sieves prepared as described herein can have a small crystal size. The crystal size is based on individual crystals (including twinned crystals) but does not include agglomerations of crystals. Crystal size is the length of longest diagonal of the three-dimensional crystal. Direct measurement of the crystal size can be performed using microscopy methods, such as SEM and TEM. For example, measurement by SEM involves examining the morphology of materials at high magnifications (typically 1000× to 10,000×). The SEM method can be performed by distributing a representative portion of the molecular sieve powder on a suitable mount such that individual particles are reasonably evenly spread out across the field of view at 1000× to 10,000× magnification. From this population, a statistically significant sample of random individual crystals (e.g., 50 to 200) are examined and the longest diagonal of the individual crystals are measured and recorded. (Particles that are clearly large polycrystalline aggregates should not be included the measurements.) Based on these measurements, the arithmetic mean of the sample crystal sizes is calculated.

The TON framework type molecular sieves synthesized as described herein are characterized by their powder X-ray diffraction (XRD) pattern. Powder XRD patterns representative of TON framework type molecular sieves can be referenced in "*Collection of Simulated XRD Powder Patterns for Zeolites*" by M. M. J. Treacy and J. B. Higgins (Elsevier, Fifth Revised Edition, 2007).

The X-ray diffraction data reported herein were collected by standard techniques using copper K-alpha radiation. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

Hydroisomerization of Paraffinic Hydrocarbon Feedstocks

The present molecular sieve is suitable for use as a catalyst in hydroisomerizing paraffinic hydrocarbon feedstocks when contacted by the catalyst with hydrogen at hydroisomerization conditions to yield a product having an increase in branched hydrocarbons relative to hydrocarbon feedstock.

Hydroisomerization conditions include a temperature of from 200° C. to 450° C. (e.g., 250° C. to 400° C.), a pressure of from 0.5 to 20 MPa (e.g., 1 to 15 MPa), a liquid hourly space velocity of from 0.1 to 10 $h^{-1}$ (e.g., 0.5 to 5 $h^{-1}$), and a hydrogen circulation rate of from 35.6 to 1781 $Nm^3/m^3$ (e.g., 890 to 1424 $Nm^3/m^3$).

The hydrocarbon feedstock is not limited to a specific type if the hydrocarbon feedstock includes n-C8+ hydrocarbons (e.g., n-C10+ hydrocarbons, or n-C15+ hydrocarbons). More specifically, examples of such hydrocarbon feedstocks include relatively light distilled fractions, such as kerosenes and jet fuels; and high boiling point stocks, such as fuel fractions or wax fractions derived from any type of crude oils, atmospheric distillation residues (atmospheric residues), vacuum tower residues, vacuum distillation residues (vacuum residues), cycle stocks, syncrudes (e.g., shale oil, tar oil, and the like), gas oil, vacuum gas oil, foots oil, and Fischer-Tropsch synthetic oil; and other heavy oils.

EXAMPLES

The following illustrative examples are intended to be non-limiting.

Example 1

In a 23 mL Teflon autoclave 3.96 g of an aqueous solution of 1,3,4-trimethylimidazolium hydroxide (0.98 mmol $OH^-$/g) was mixed with 5.21 g of deionized water. Then, 1.0 g of CBV780 Y zeolite (SAR=80) was added, followed by seeds of zeolite TON, and mixed well. The sealed autoclave was heated at 170° C. for 3 days with rotation at 43 rpm. The material was recovered by filtration and washed with copious amounts of water and finally dried in air at 85° C.

The material was calcined in air by placing a thin bed of material in a calcination dish and heated in a muffle furnace from room temperature to 120° C. at a rate of 1° C./minute and held at 120° C. for 2 hours. Then, the temperature was ramped up to 540° C. at a rate of 1° C./minute and held at 540° C. for 5 hours. The temperature was ramped up again at 1° C./minute to 595° C. and held 595° C. for 5 hours. The material was then allowed to cool to room temperature.

Figure 2A:
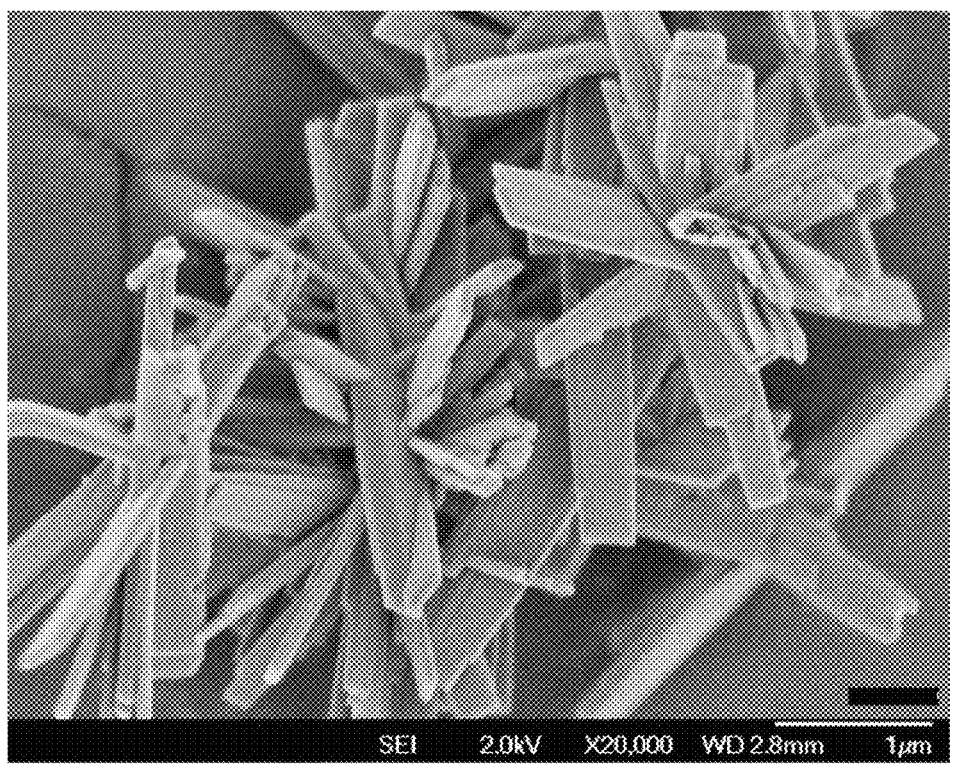
FIGS. 2(A) and 2(B) show illustrative Scanning Electron Micrograph (SEM) images of the product of Example 1 at various magnifications.
Figure 2B:
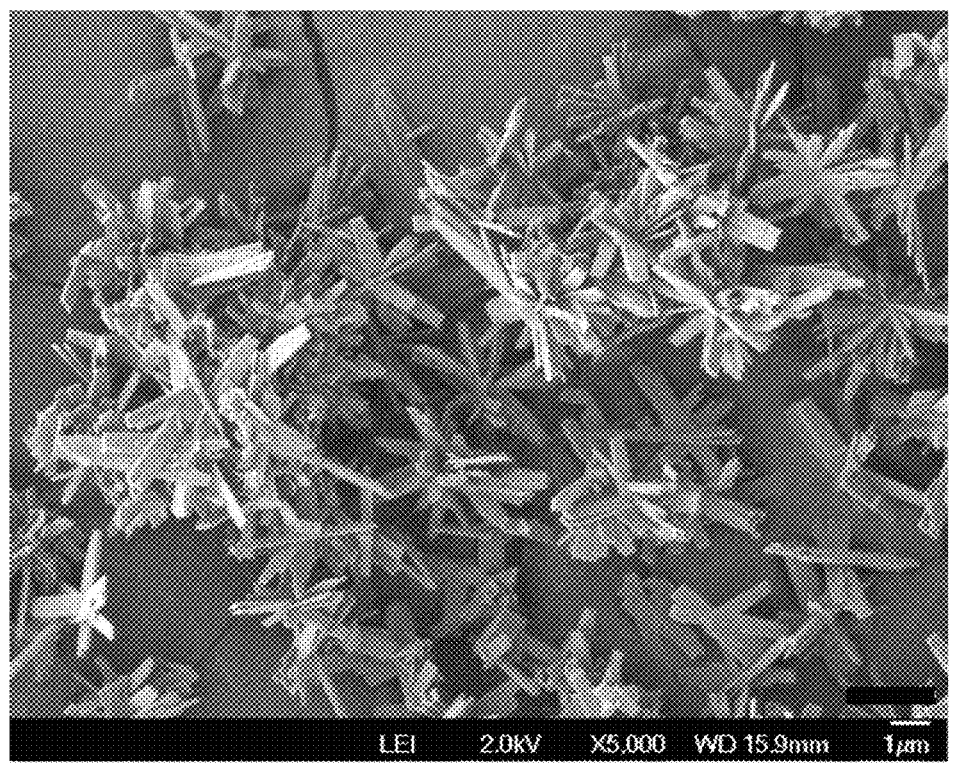

The powder XRD pattern of the calcined material is shown in FIG. 1 and indicates that the material is a TON framework zeolite. FIGS. 2(A) and 2(B) show illustrative SEM images of the product at various magnifications. As shown, the crystals have a columnar morphology with an average length greater than 1 µm, an average width of about 0.5 µm, and an average thickness of less than 0.1 µm.

Example 2

In a 23 mL Teflon autoclave 0.72 g of an aqueous solution of 1,3,4-trimethylimidazolium hydroxide (0.98 mmol $OH^-$/g) was mixed with 0.17 g of $LiOH \cdot H_2O$ and 7.22 g of deionized water. Then, 4.0 g of an alumina-coated silica (SAR=100, 26.5% solids, Nalco) was added, followed by seeds of zeolite TON, and mixed well. The sealed autoclave was heated at 170° C. for 3 days with rotation at 43 rpm. The material was recovered by filtration and washed with copious amounts of water and finally dried in air at 85° C.

The as-synthesized material was calcined according to the method described in Example 1.

Figure 3:
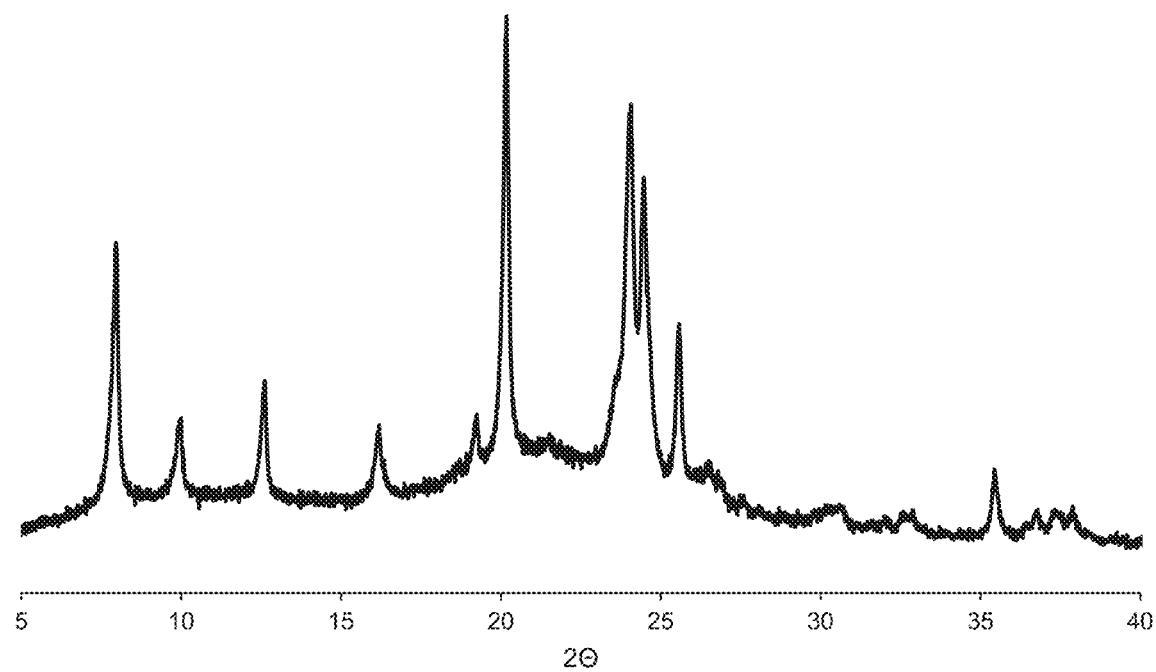
FIG. 3 shows a powder XRD pattern of the calcined molecular sieve obtained in Example 2.
Figure 4A:
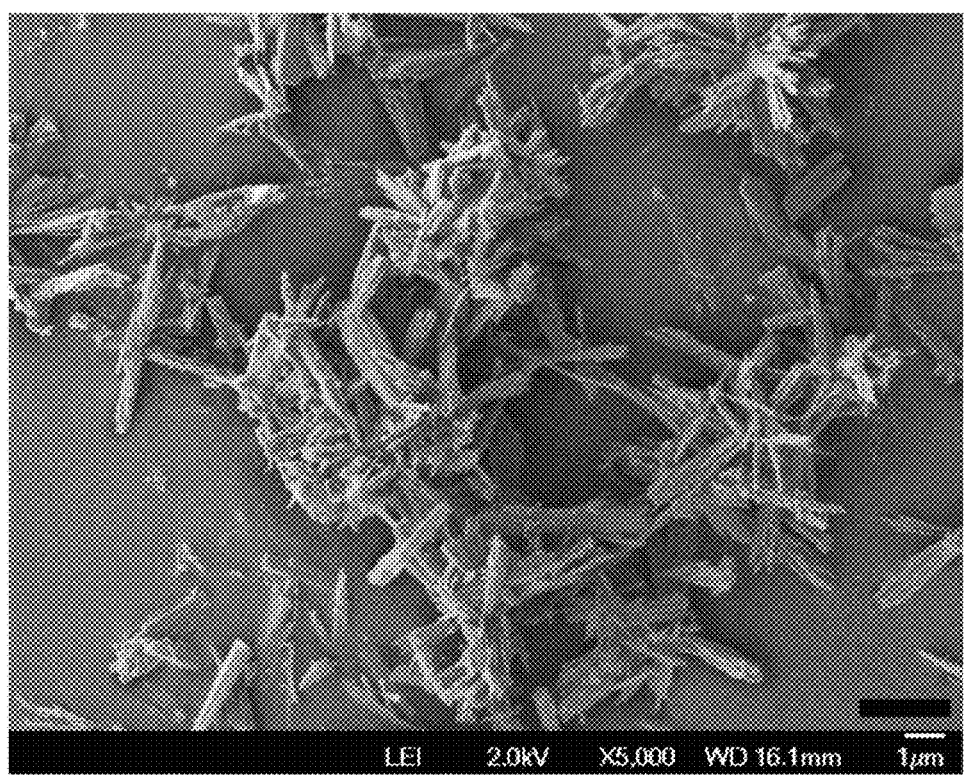
FIGS. 4(A) and 4(B) show illustrative SEM images of the product of Example 2 at various magnifications.
Figure 4B:
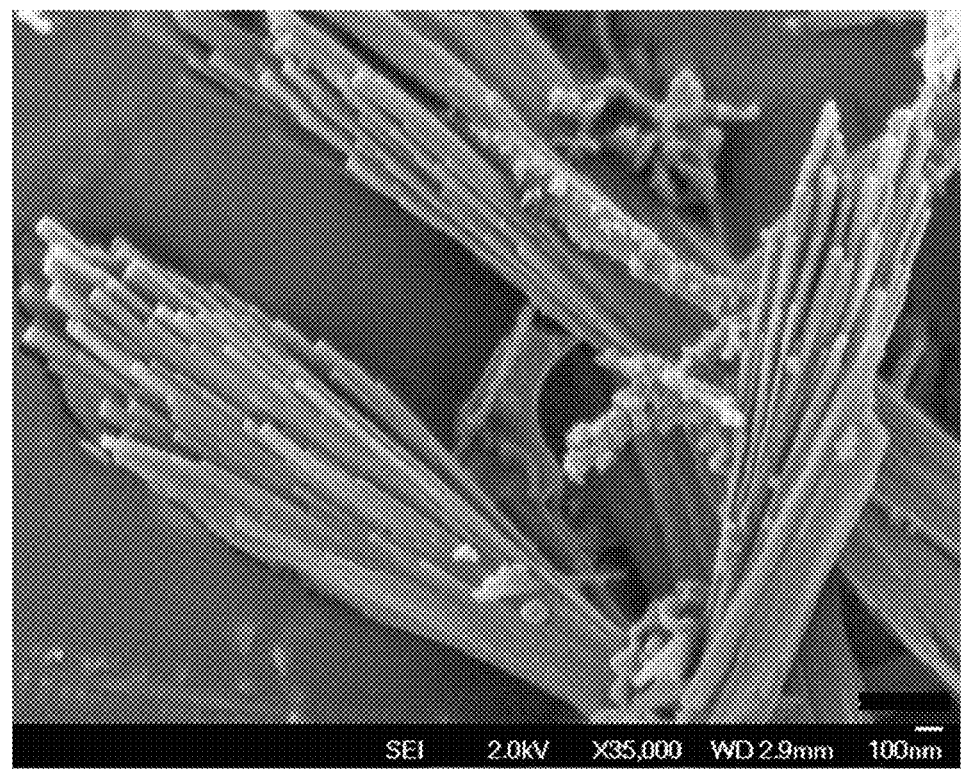

The powder XRD pattern of the calcined material is shown in FIG. 3 and indicates that the material is a TON framework zeolite. FIGS. 4(A) and 4(B) show illustrative SEM images of the product at various magnifications. As shown, the crystals were in the form of bundles of needles having a mean length greater than 1 µm and a mean thickness of less than 0.1 nm.

Example 3

In a 23 mL Teflon autoclave 0.72 g of an aqueous solution of 1,3,4-trimethylimidazolium hydroxide (0.98 mmol $OH^-$/g) was mixed with 0.096 g of $LiOH \cdot H_2O$, 1.76 g of 1 M KOH and 5.54 g of deionized water. Then, 4.0 g of an alumina-coated silica (SAR=100, 26.5% solids, Nalco) was added, followed by seeds of zeolite TON, and mixed well. The sealed autoclave was heated at 170° C. for 3 days with rotation at 43 rpm. The material was recovered by filtration and washed with copious amounts of water and finally dried in air at 85° C.

The as-synthesized material was calcined according to the method described in Example 1.

Figure 5:
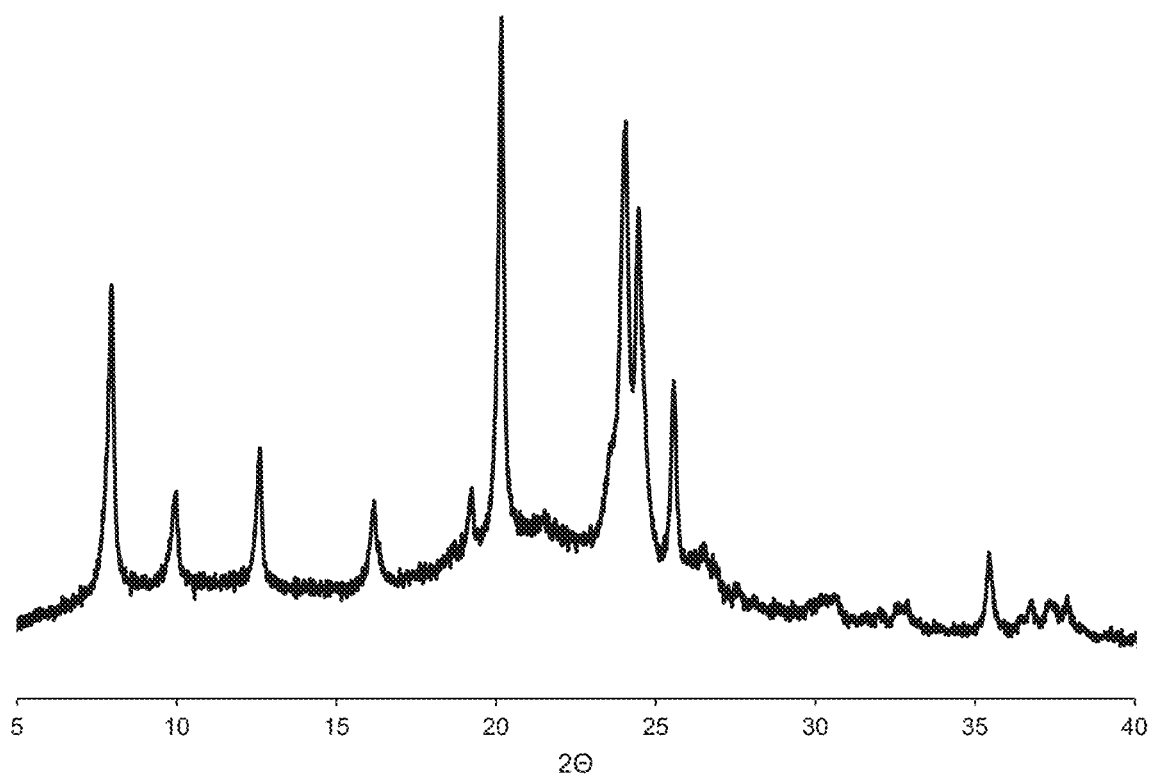
FIG. 5 shows a powder XRD pattern of the calcined molecular sieve obtained in Example 3.
Figure 6A:
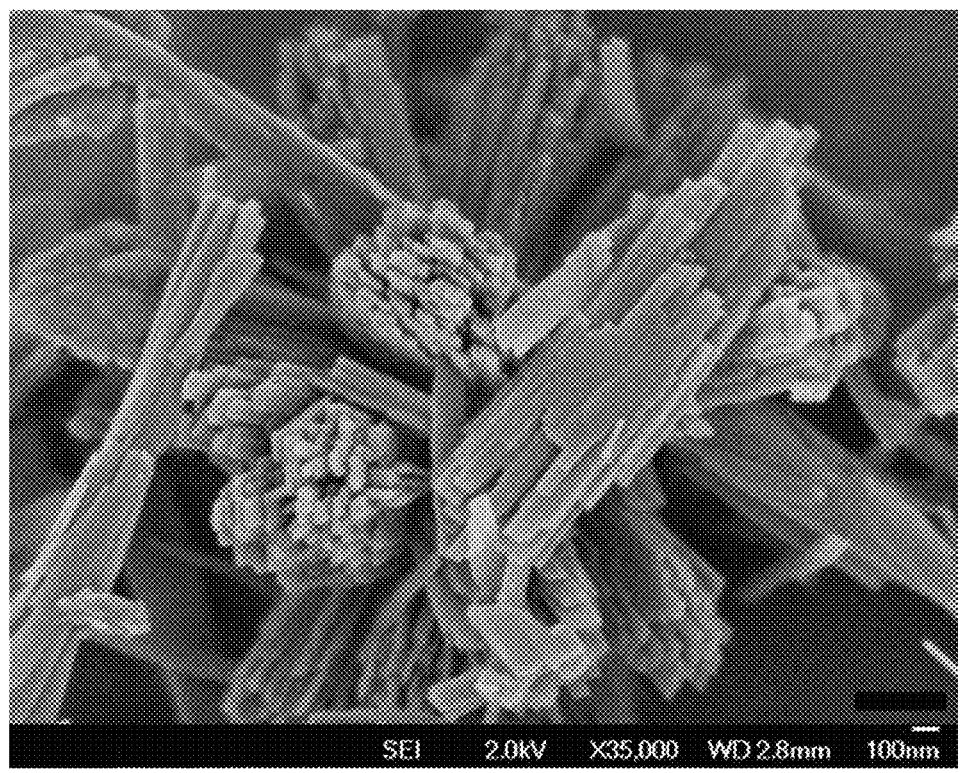
FIGS. 6(A) and 6(B) show illustrative SEM images of the product of Example 3 at various magnifications.
Figure 6B:
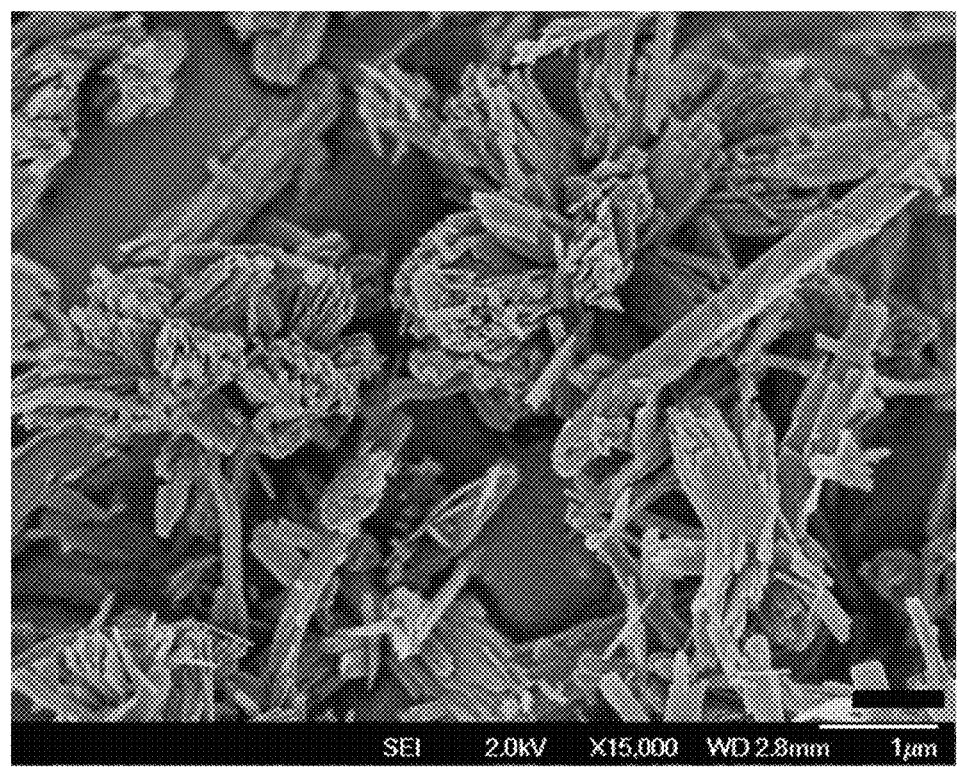

The powder XRD pattern of the calcined material is shown in FIG. 5 and indicates that the material is a TON framework zeolite. FIGS. 6(A) and 6(B) show illustrative SEM images of the product at various magnifications. As shown, the crystals were in the form of columnar bundled needles with an average length greater than 1 µm, an average width of about 0.1 µm, and an average thickness of less than 100 nm.

Example 4

In a 23 mL Teflon autoclave 1.91 g of an aqueous solution of 1,3,4-trimethylimidazolium hydroxide (0.98 mmol $OH^-$/g) was mixed with 0.085 g of $LiOH \cdot H_2O$ and 3.42 g of deionized water. Then 1.0 g of CBV780 Y zeolite (SAR=80) was added, followed by seeds of zeolite TON, and mixed well. The sealed autoclave was heated at 150° C. for 3 days with rotation at 43 rpm. The material was recovered by filtration and washed with copious amounts of water and finally dried in air at 85° C.

The as-synthesized material was calcined according to the method described in Example 1.

Figure 7:
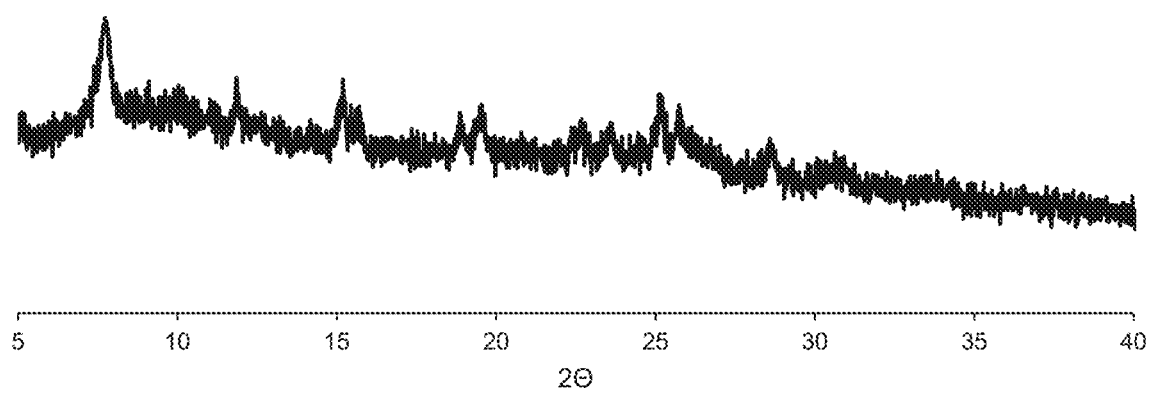
FIG. 7 shows a powder XRD pattern of the calcined molecular sieve obtained in Example 4.
Figure 8A:
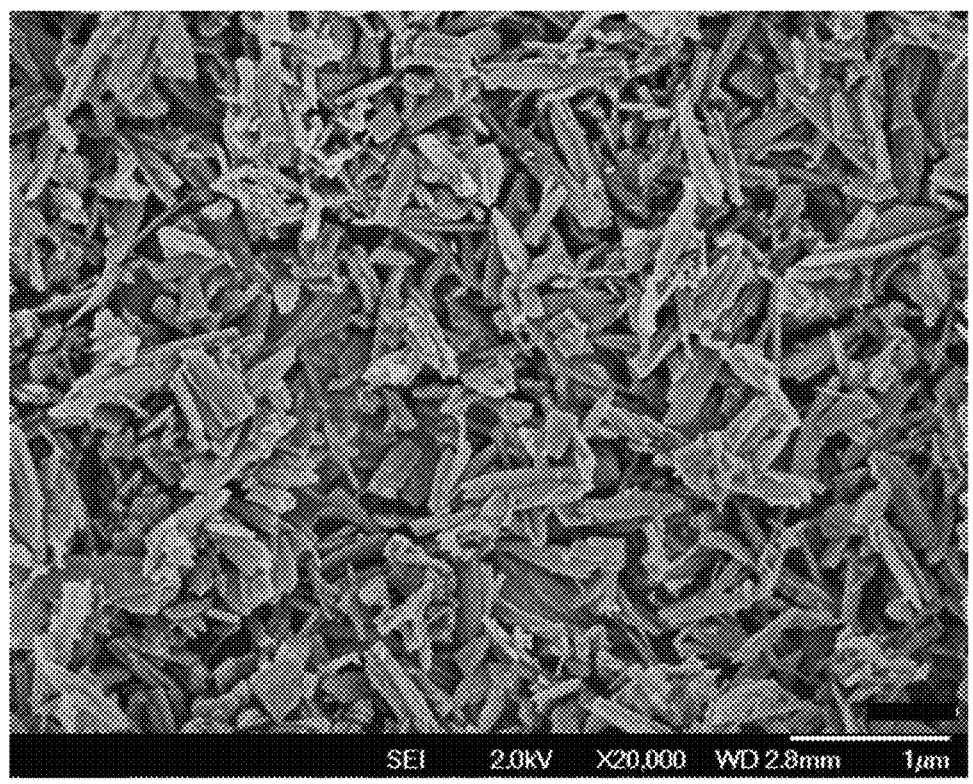
FIGS. 8(A) and 8(B) show illustrative SEM images of the product of Example 4 at various magnifications.
Figure 8B:
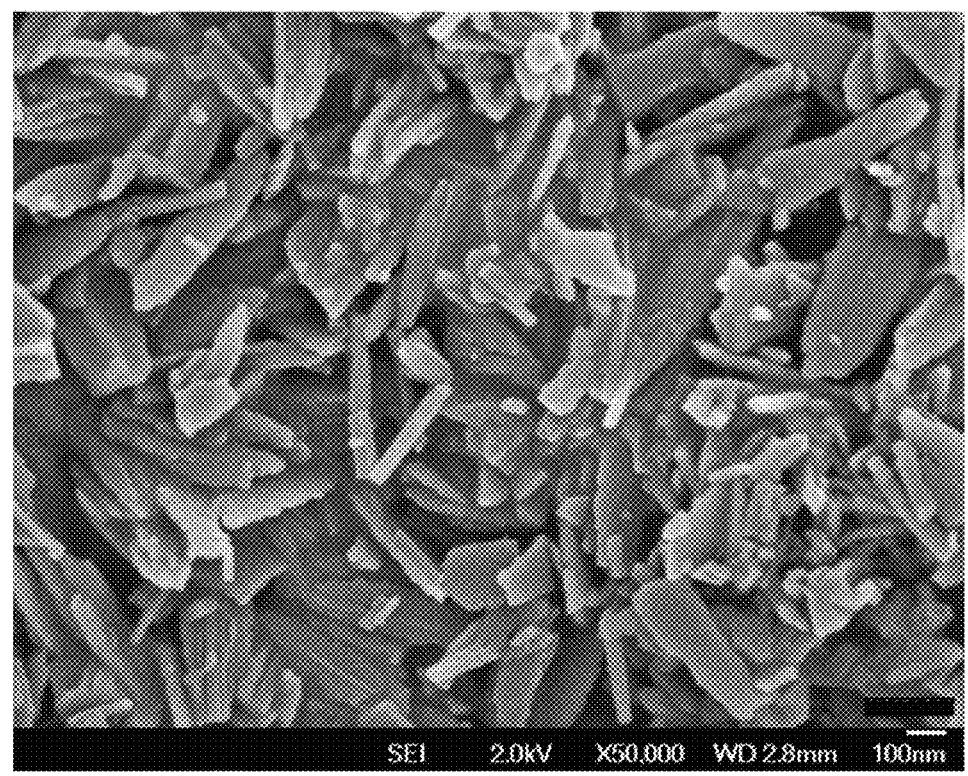

The powder XRD pattern of the calcined material is shown in FIG. 7 and indicates that the material is a TON framework zeolite. FIGS. 8(A) and 8(B) show illustrative SEM images of the product at various magnifications. As shown, the crystals were in the form of irregularly shaped platelets with mean dimensions of less than 1 µm×1 µm and a mean thickness of less than 50 nm.

Example 5

In a 125 mL Teflon autoclave 5.38 g of an aqueous solution of 1,3,4-trimethylimidazolium hydroxide (0.88 mmol $OH^-$/g) was mixed with 27.24 g of 1 M KOH and 21.2 g of deionized water. Then, 21.0 g of an alumina-coated silica (SAR=35; 24.5% solids, Nalco) was added and then 7.02 g of LUDOX® AS-30 colloidal silica, followed by seeds of zeolite TON, and mixed well. The sealed autoclave was heated at 175° C. for 2 days with rotation at 43 rpm. The material was recovered by filtration and washed with copious amounts of water and finally dried in air at 85° C.

The as-synthesized material was calcined according to the method described in Example 1.

Figure 9:
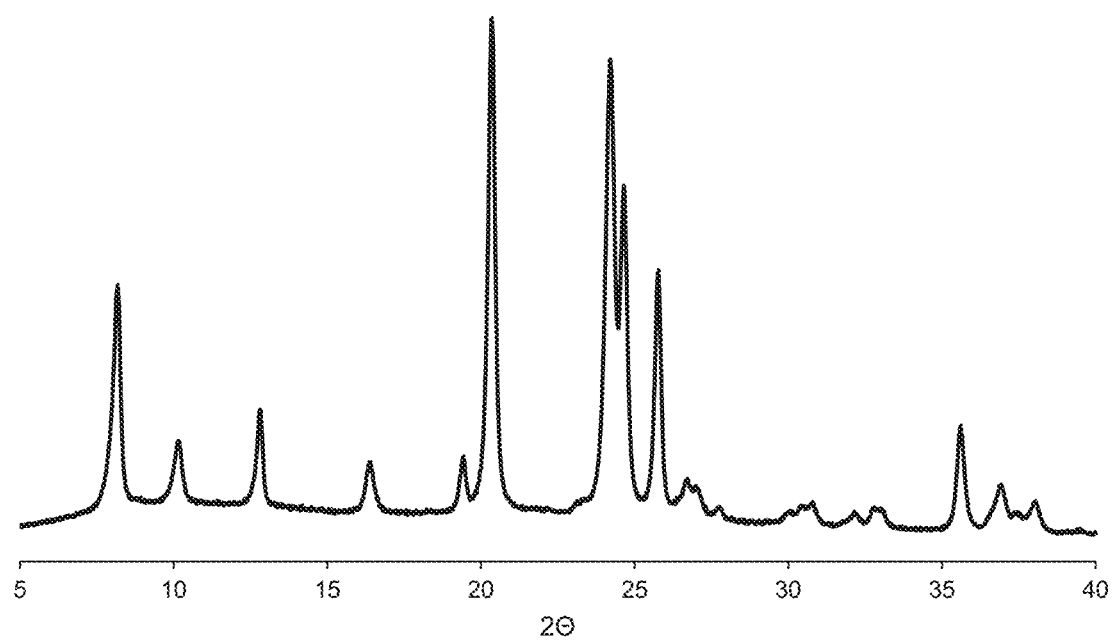
FIG. 9 shows a powder XRD pattern of the calcined molecular sieve obtained in Example 5.
Figure 10:
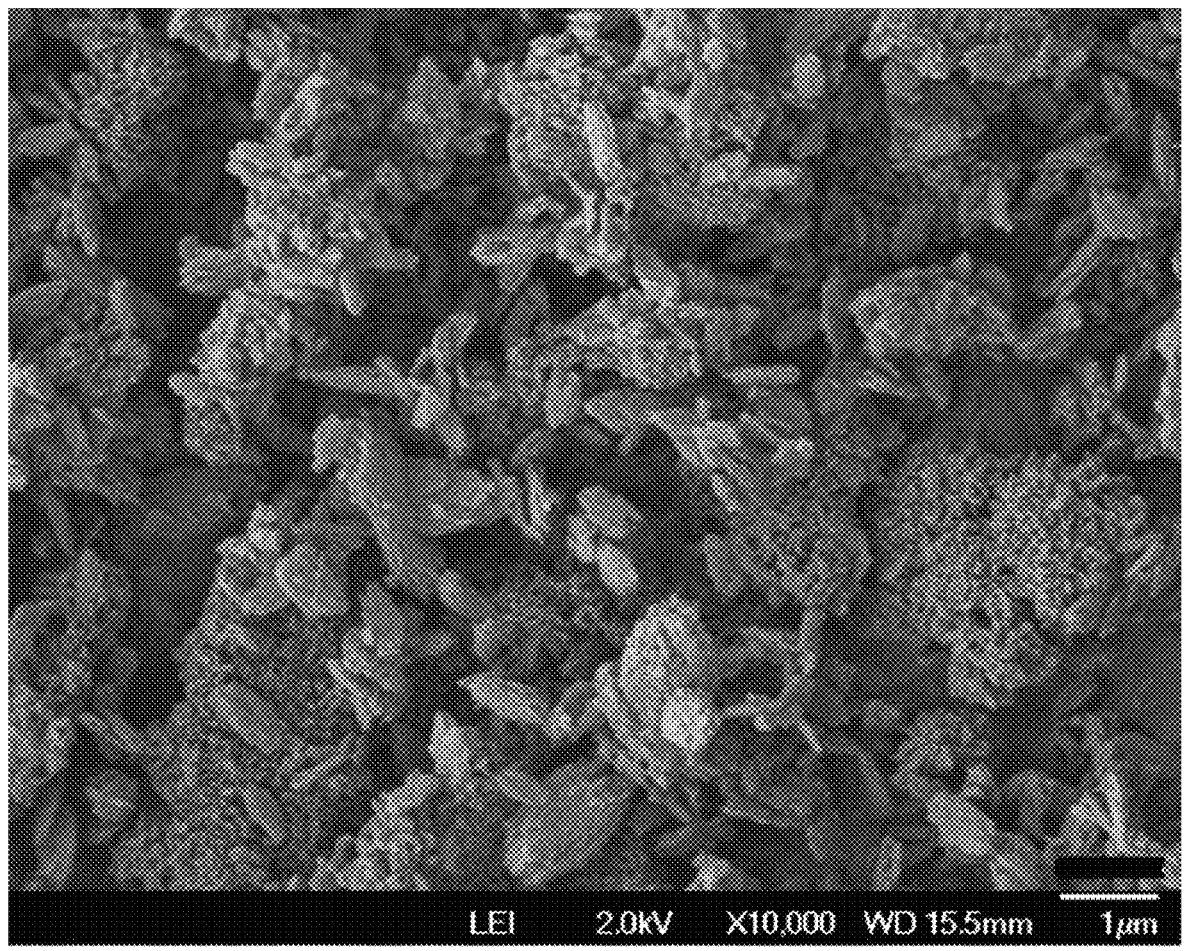
FIG. 10 shows an illustrative SEM image of the product of Example 5.

The powder XRD pattern of the calcined material is shown in FIG. 9 and indicates that the material is a TON framework zeolite. FIG. 10 shows an illustrative SEM image of the product. As shown, crystals were in the form of a bundle of fibrous needles of small crystal size.

The calcined material was then converted to the ammonium form by heating in a solution of ammonium nitrate (typically, 1 g $NH_4NO_3$/1 g zeolite in 10 mL of $H_2O$ at 85° C. for at least 3 hours). The material was then filtered. This was repeated twice for a total of 3 exchanges. At the end, the material was washed with deionized water to a conductivity of less than 100 µS/cm dried in air at 85° C.

The acid site density was characterized using n-propylamine temperature-programmed desorption (TPD) and found to be 522 µmol $H^+$/g.

The nitrogen micropore volume was found to be 0.095 $cm^3/g$ (t-plot analysis) and the BET surface area was 232.6 $m^2/g$.

The SAR was of the material found to be 44.7, according to Inductively Coupled Plasma-Mass Spectrometry (ICP-MS).

For the palladium exchange to 0.5 wt. % Pd, 1.6 g of $NH_4^+$ form material was combined with 15.3 g of deionized water and 7.0 g of 0.156 N $NH_4OH$ solution followed by 1.6 g of palladium solution that was prepared by combining 0.36 g of $Pd(NH_3)_4(NO_3)_2$ in 21 g of deionized water and 3 g of 0.148N $NH_4OH$ solution. The pH was then checked, and if necessary, adjusted to 10 by adding concentrated ammonium hydroxide dropwise until a pH of 10 was reached. After standing at room temperature for 3 days, the pH was checked again and if necessary readjusted to 10 and allowed to sit for 1 more day. The material was recovered by filtration, washed with deionized water, and dried in air overnight at 85° C. The Pd form material was calcined in dry air by heating at 1° C./minute ramp to 120° C. and held for 180 minutes at 120° C., and then heated at 1° C./minute to 482° C. and held for 180 minutes at 482° C. Finally, the material was pelletized at 5 kpsi, crushed and sieved to 20-40 mesh.

Example 6

In a 125 mL Teflon autoclave 5.37 g of an aqueous solution of 1,3,4-trimethylimidazolium hydroxide (0.88 mmol OH⁻/g) was mixed with 27.18 g of 1 M KOH and 20.1 g of deionized water. Then 29.0 g of an alumina-coated silica (SAR=80; 26.9% solids, Nalco) was added, followed by seeds of zeolite TON, and mixed well. The sealed autoclave was heated at 175° C. for 2 days at a rotation of 43 rpm. The material was recovered by filtration and washed with copious amounts of water and finally dried in air at 85° C.

The material was calcined and converted to ammonium form according to the method described in Example 5.

Figure 11:
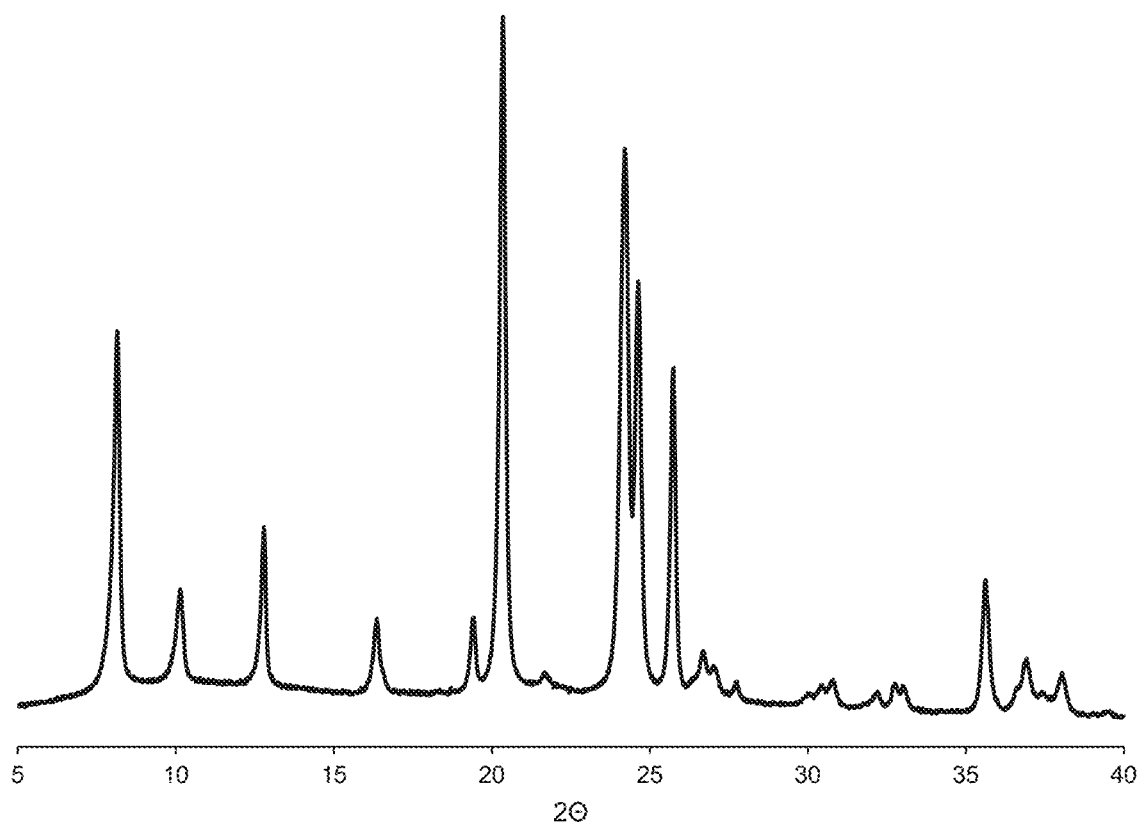
FIG. 11 shows a powder XRD pattern of the calcined molecular sieve obtained in Example 6.
Figure 12A:
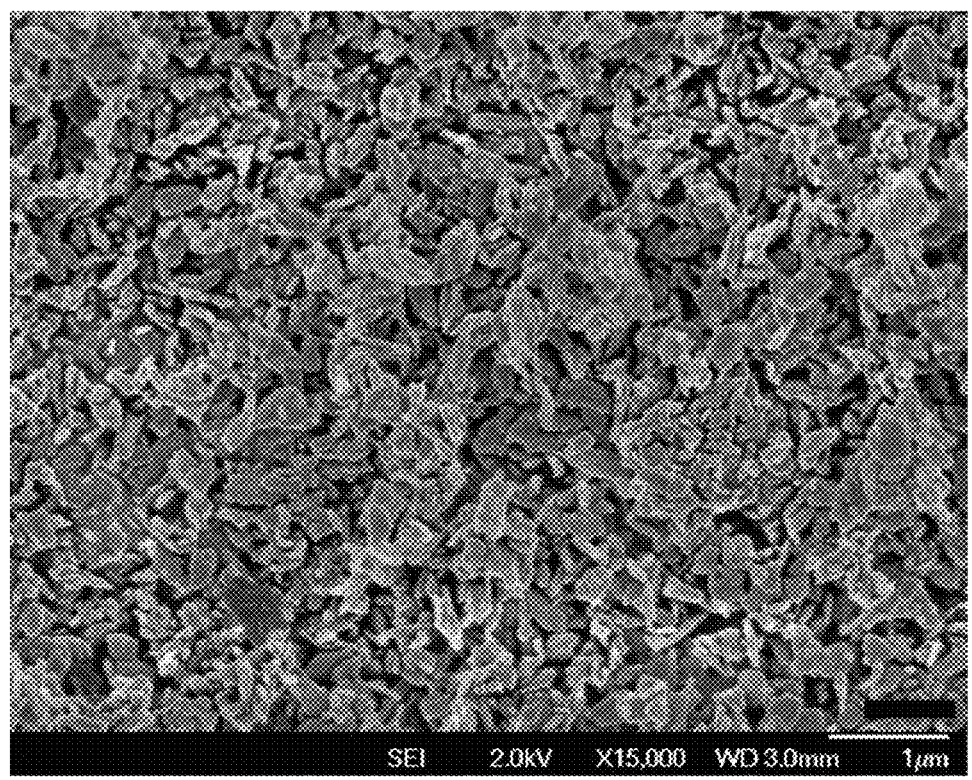
FIGS. 12(A) and 12(B) show illustrative SEM images of the product of Example 6 at various magnifications.
Figure 12B:
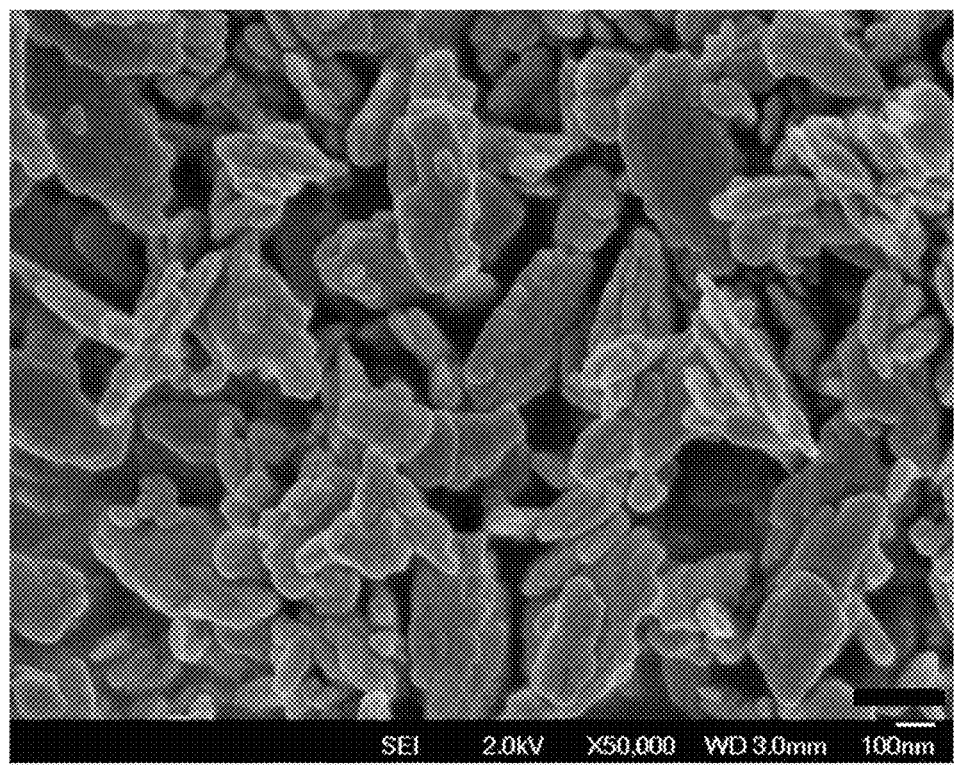
Figure 13:
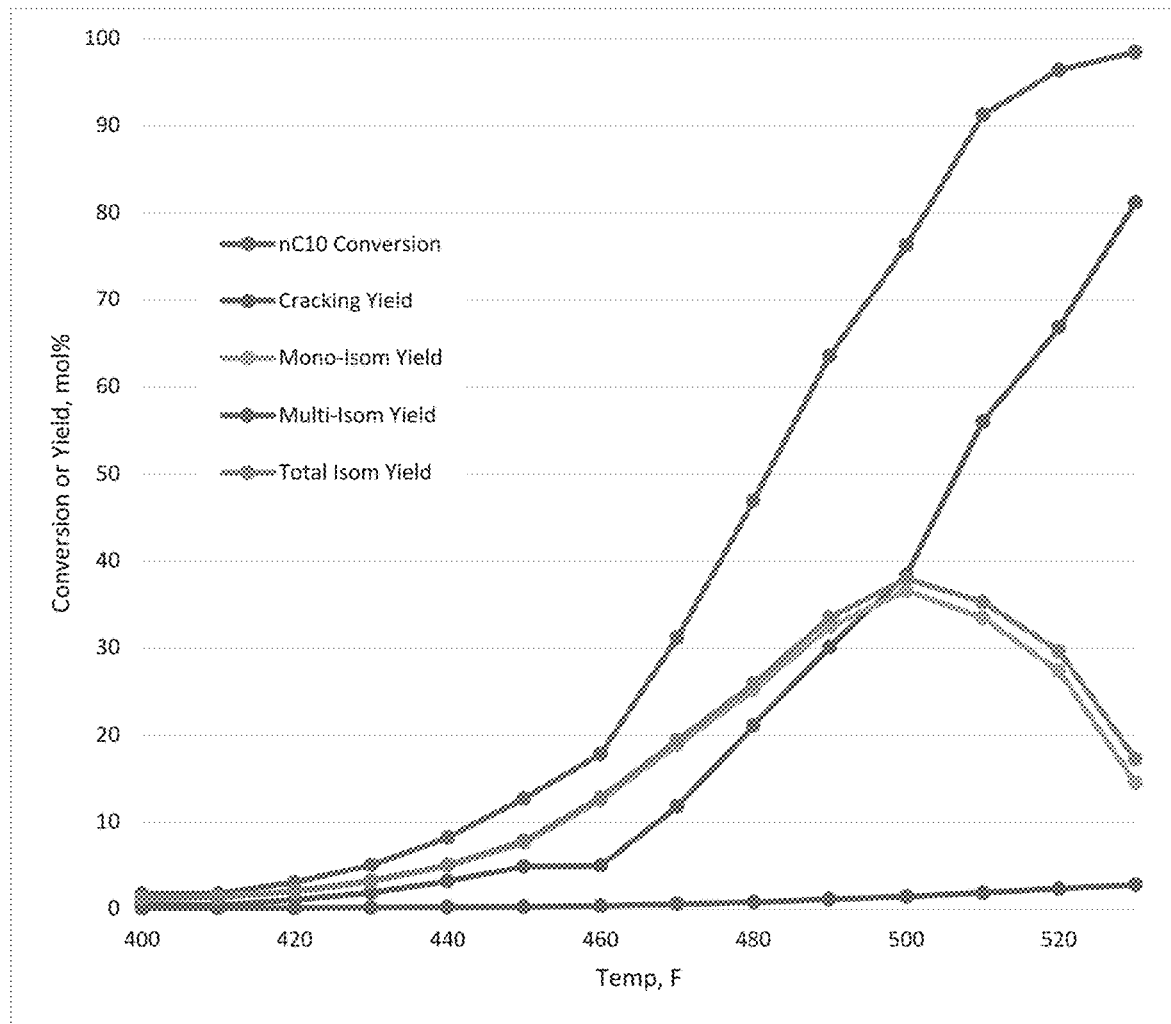
FIG. 13 is a plot of conversion as a function of temperature for n-decane conversion over the catalyst of Example 5.
Figure 14:
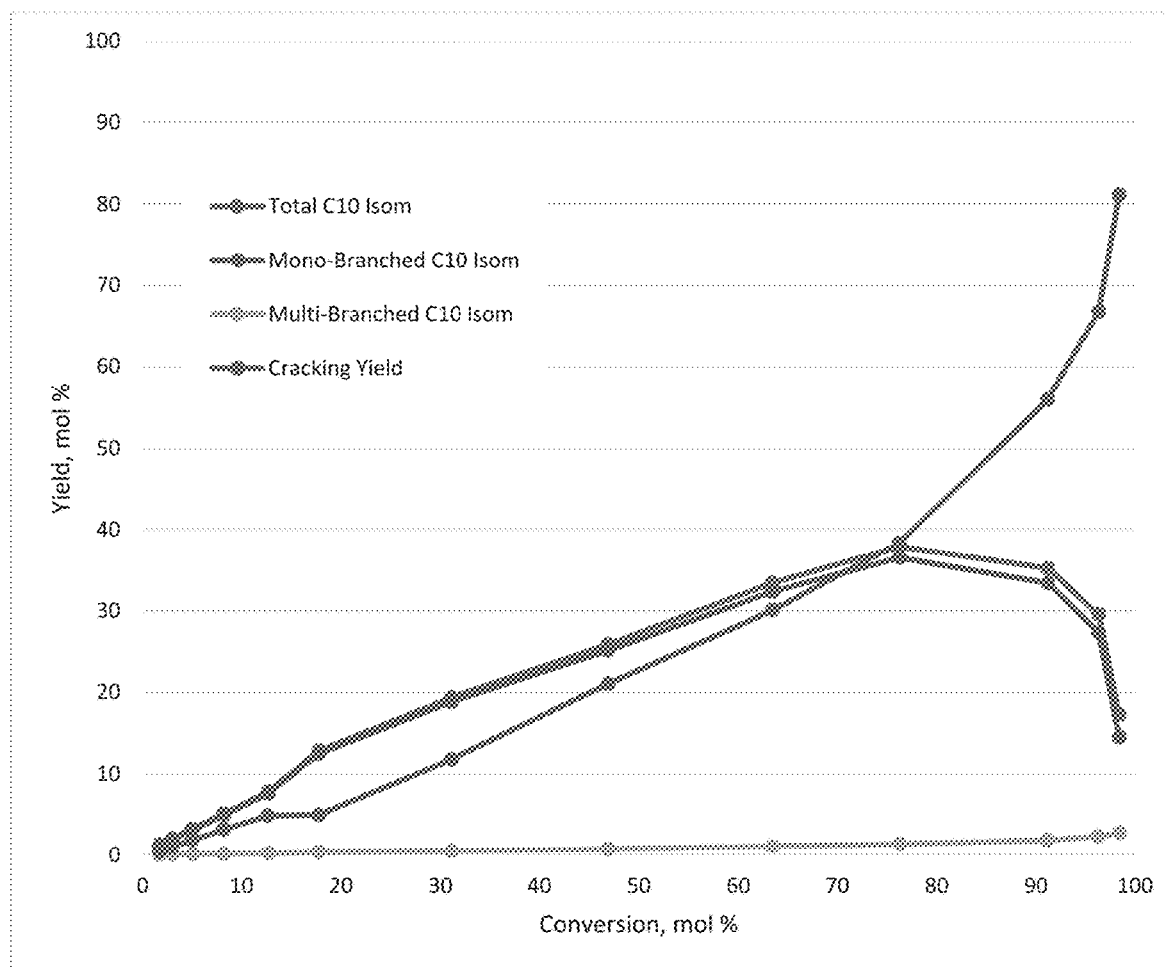
FIG. 14 is a plot of conversion versus yield for n-decane conversion over the catalyst of Example 5.
Figure 15:
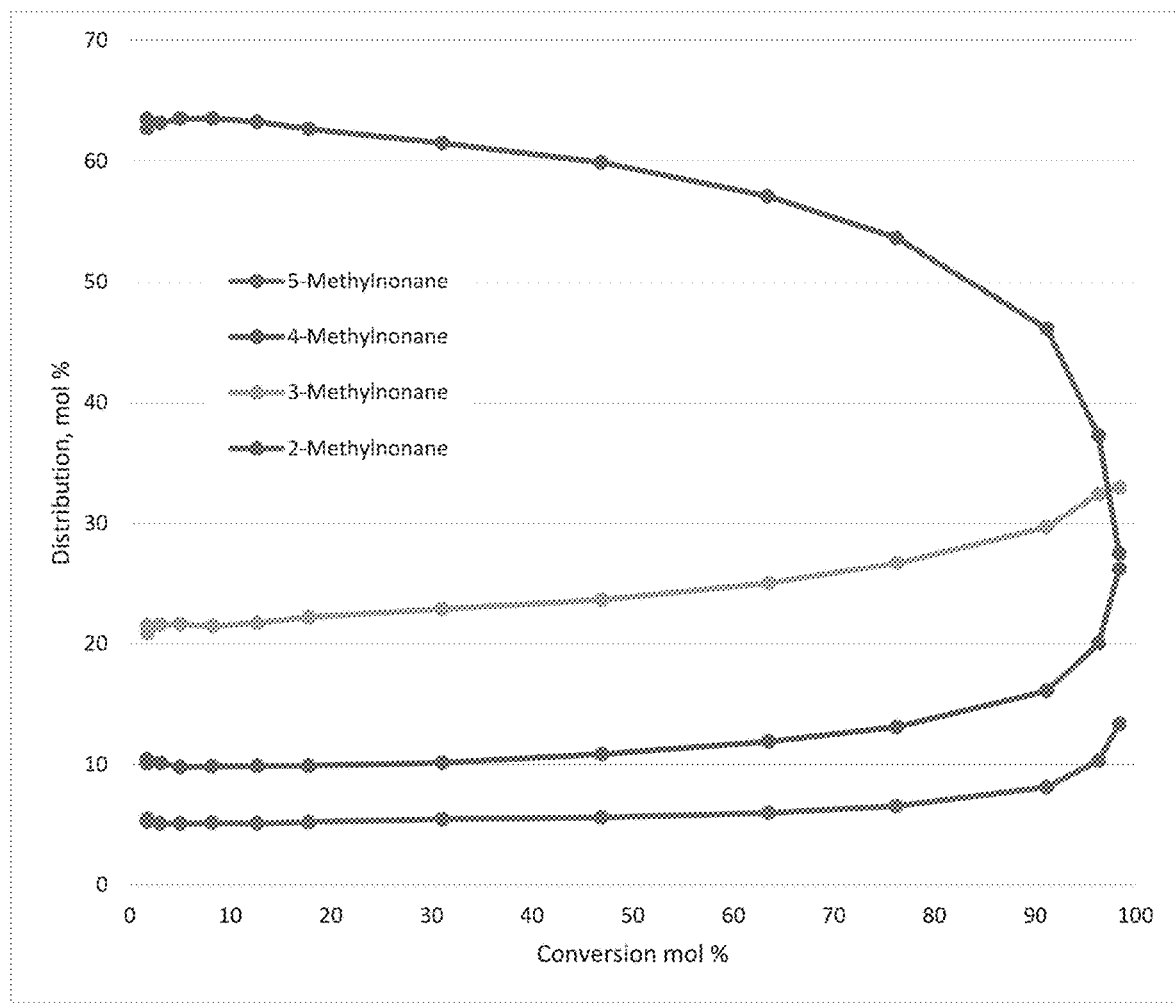
FIG. 15 is plot illustrating the distribution of methylnonane isomers as a function of conversion for n-decane conversion over the catalyst of Example 5.
Figure 16:
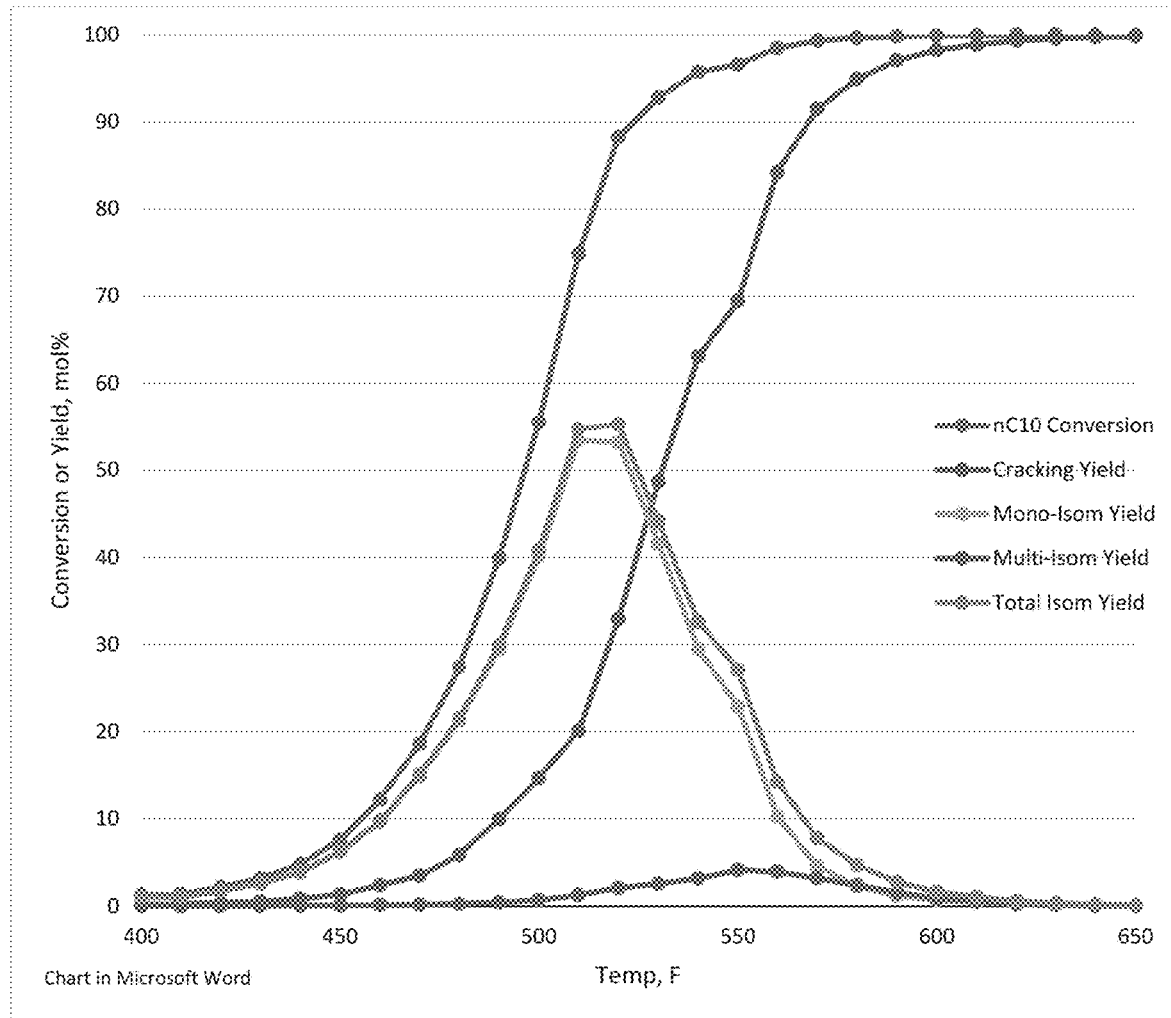
FIG. 16 is a plot of conversion as a function of temperature for n-decane conversion over the catalyst of Example 6.
Figure 17:
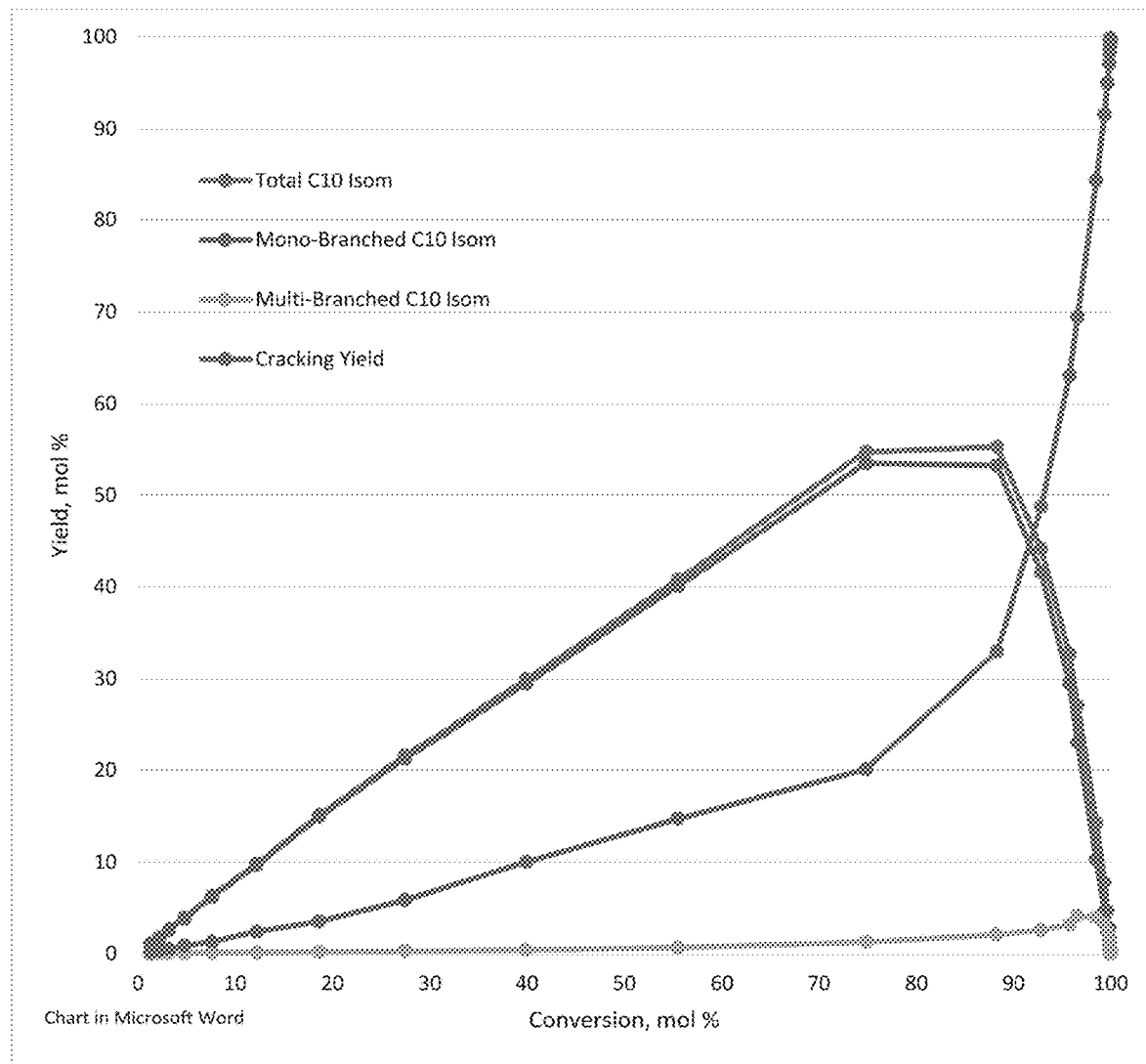
FIG. 17 is a plot of conversion versus yield for n-decane conversion over the catalyst of Example 6.
Figure 18:
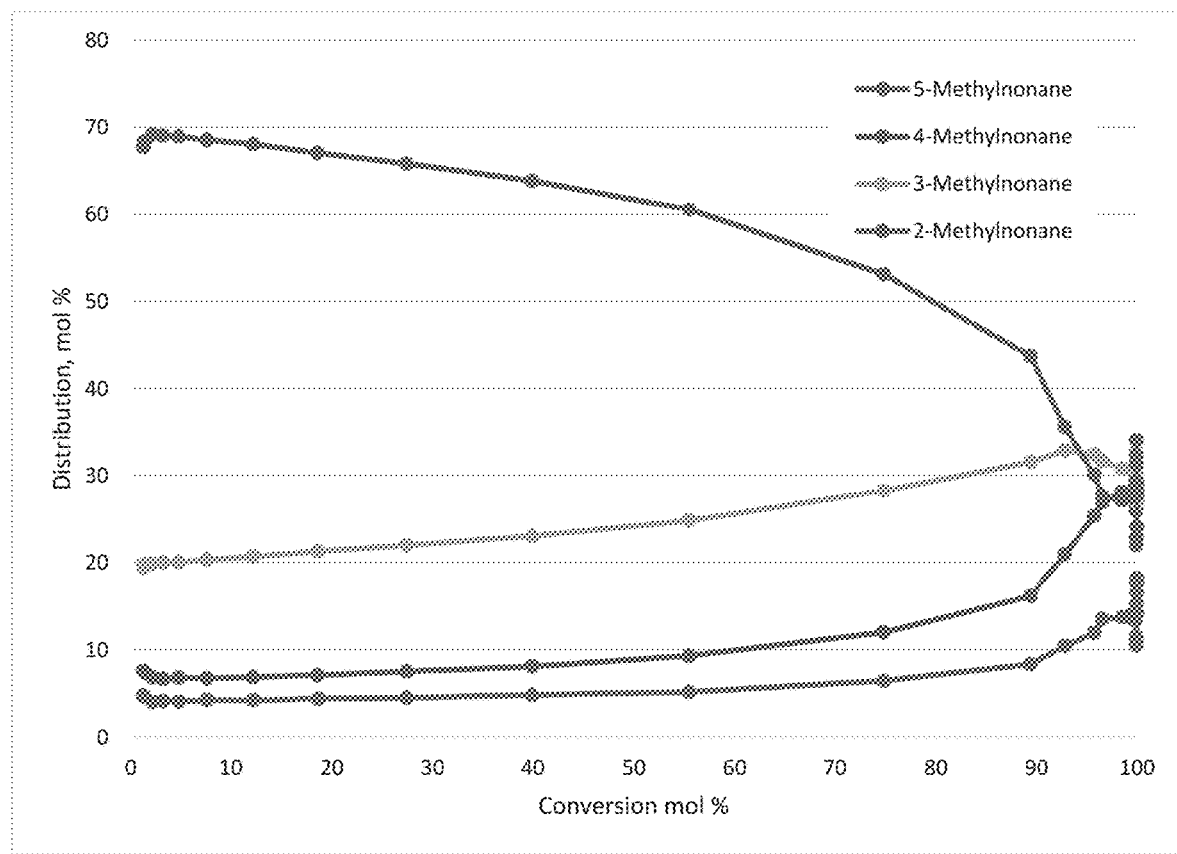
FIG. 18 is plot illustrating the distribution of methylnonane isomers as a function of conversion for n-decane conversion over the catalyst of Example 6.

The powder XRD pattern of the calcined material is shown in FIG. 11 and indicates that the material is a TON framework zeolite. FIGS. 12(A) and 12(B) show illustrative SEM images of the product at various magnifications. As shown, the crystals have a somewhat lamellar morphology with a very small crystal size.

The acid site density was characterized using n-propylamine TPD and found to be 340 μmol H⁺/g.

The nitrogen micropore volume was found to be 0.10 cm³/g (t-plot analysis) and the BET surface area was 240.1 m²/g.

The SAR was of the material found to be 70.1, according to ICP-MS.

Exchange to 0.5 wt. % Pd was conducted according to the method described in Example 5.

Example 7

Hydroconversion of n-Hexadecane 0.5 g of the palladium exchanged sample was loaded in the center of a 23 inch-long×0.25 inch outside diameter stainless steel reactor tube with alundum loaded upstream of the catalyst for pre-heating the feed (total pressure of 1200 psig; down-flow hydrogen rate of 160 mL/minute, when measured at 1 atmosphere pressure and 25° C.; down-flow liquid feed rate of 1 mL/hour). All materials were first reduced in flowing hydrogen at about 315° C. for 1 hour. Products were analyzed by on-line capillary gas chromatography (GC) once every thirty minutes. Raw data from the GC was collected by an automated data collection/processing system and hydrocarbon conversions were calculated from the raw data.

Conversion was defined as the amount of n-hexadecane reacted to produce other products (including iso-C16 isomers). Yields were expressed as weight percent of products other than n-C16 and included iso-C16 as a yield product. The results at 96% conversion are reported in Table 3.

TABLE 3

Summary of n-Hexadecane Hydroconversion at 96% Conversion

|  | Catalyst | |
| --- | --- | --- |
|  | Example 5 | Example 6 |
| Selectivity | 64.4 | 67.7 |
| Temperature [° F.] | 514.5 | 522.5 |
| C4- Cracking [wt. %] | 7.3 | 4.3 |

Example 8

Hydroconversion of n-Decane

For catalytic testing, 0.5 g of the Pd catalyst (weight of the dehydrated sample as determined by thermogravimetric analysis at 600° C.) was loaded in the center of a 23 inch-long×0.25 inch outside diameter stainless steel reactor tube with alundum loaded upstream of the catalyst for preheating the feed (a total pressure of 1200 psig; a down-flow hydrogen rate of 12.5 mL/minute, when measured at 1 atmosphere pressure and 25° C.; and a down-flow liquid feed rate of 1 mL/hour). The catalyst was first reduced in flowing hydrogen at 315° C. for 1 hour. The reaction was carried out at a temperature of from 230° C. to 310° C. Products were analyzed by on-line capillary GC approximately once every sixty minutes. Raw data from the GC was collected by an automated data collection/processing system and hydrocarbon conversions were calculated from the raw data. Conversion is defined as the amount n-decane reacted in mol % to produce other products (including iso-C10). The yield of iso-C10 is expressed as mole percent of products other than n-decane. The yield of cracking products (smaller than C10) is expressed as mole percent of n-decane converted to cracking products. The results are shown in FIG. 13 through FIG. 18, and the key catalytic performance metrics are in Table 4.

The Modified Constraint Index (CI*) was calculated as the ratio of 2-methylnonane to 5-methylnonane at the total isomer yield of around 5% and is shown in Table 4.

TABLE 4

Summary of n-Decane Hydroconversion at Maximum Total Isomer Yield

|  | Catalyst | |
| --- | --- | --- |
|  | Example 5 | Example 6 |
| Temp. at Maximum Isomer Yield [° F.] | 500 | 520 |
| Maximum Total Isomer Yield [%] | 37.9 | 55.3 |
| Mono-Isomer Yield [%] | 36.5 | 53.2 |
| Cracking [%] | 38.3 | 33.0 |
| Conversion [%] | 76.2 | 88.3 |
| CI* | 12.3 | 16.0 |

The invention claimed is:

1. A pure phase molecular sieve of TON framework having a molar ratio of $SiO_2/Al_2O_3$ in a range of from 30 to 100 and, in its as-synthesized form, consisting of 1,3,4-trimethylimidazolium cations and optionally an alkali metal cation in its pores.

2. The molecular sieve of claim 1, having a molar ratio of $SiO_2/Al_2O_3$ in a range of from 35 to 80.

3. The molecular sieve of claim 1, wherein the crystals of the molecular sieve have a columnar morphology with an average length greater than 1 um, an average width of about 0.5 μm, and an average thickness of less than 0.1 μm.

4. The molecular sieve of claim 1, wherein the crystals of the molecular sieve are in a form of columnar bundled needles with an average length greater than 1 μm, an average width of about 0.1 μm, and an average thickness of less than 100 nm.

5. The molecular sieve of claim 1, wherein the alkali metal is selected from the group consisting of lithium, sodium, potassium, and any combinations thereof.

* * * * *